United States Patent [19]

Thompson

[11] Patent Number: 4,938,898

[45] Date of Patent: Jul. 3, 1990

[54] ALPHA CHLORINATION PROCESS EMPLOYING ANTIOXIDANTS

[75] Inventor: James E. Thompson, Cincinnati, Ohio

[73] Assignee: The Procter & Gamble Company, Cincinnati, Ohio

[21] Appl. No.: 625,922

[22] Filed: Jun. 29, 1984

[51] Int. Cl.$^5$ .............................................. C11C 3/00
[52] U.S. Cl. .................................... 260/408; 562/840; 562/847; 562/857
[58] Field of Search ............... 260/408, 544 Y, 544 K, 260/694; 562/840, 847, 858

[56] References Cited

U.S. PATENT DOCUMENTS

| | | |
|---|---|---|
| 3,152,055 | 10/1964 | Katzschmann . |
| 3,584,036 | 6/1971 | Saxton et al. . |
| 3,751,461 | 8/1973 | Dhingra ..................... 260/544 Y |
| 3,880,923 | 4/1975 | Scheider et al. . |
| 4,148,811 | 4/1979 | Crawford . |
| 4,169,847 | 10/1979 | Degischer et al. ............ 260/544 Y |
| 4,368,149 | 1/1983 | Crawford . |

OTHER PUBLICATIONS

Ogata et al. (I), *Tetrahedron*, 26, pp. 5929–5937, (1970).
Ogata et al. (II), *Journal of Organic Chemistry*, 40, pp. 2960–2962, (1975).
Kirk–Othmer, *Encyclopedia of Chemical Technology*, 3rd Edition, vol. 3 (pp. 128–140) and vol. 11 (pp. 160–161), John Wiley & Sons, N.Y. (1978).
Crawford, Robert J., Journal of Organic Chemistry, 48, pp. 1364–1368, (1976).
W. Theilheimer, *Synthetic Methods of Organic Chemistry*, vol. 16, pp. 271–272, John Wiley & Sons, 1961.

*Primary Examiner*—Charles F. Warren
*Attorney, Agent, or Firm*—Leonard W. Lewis; George W. Allen; Kim W. Zerby

[57] ABSTRACT

The present invention relates to improved processes for selectively chlorinating acyl compounds at the alpha or 2-position. The process of the present invention comprises a method of producing alpha-chloro acyl chlorides comprising contacting an acyl chloride with a chlorine source at a temperature of about 75° C. to about 125° C. in the presence of (i) an effective amount of an auxiliary acidic agent and (ii) an effective amount of a food grade antioxidant and optionally (iii) an effective amount of oxygen or air.

13 Claims, No Drawings

ALPHA CHLORINATION PROCESS EMPLOYING ANTIOXIDANTS

The present invention relates to improved processes for selectively chlorinating acyl compounds at the alpha or 2-position.

BACKGROUND OF THE INVENTION

The halogenation of organic compounds at a specific site or position (regiospecific halogenation) is a very difficult task. In general, hydrocarbon compounds tend to undergo halogenation to some degree at virtually every available carbon-hydrogen linkage. The random nature of this substitution generally leads to an undesirable mixture of isomers and homologs. Further, when additional reactants are employed to make the reaction more selective or specific, additional competing reactions are also likely to be encountered; when more reactants are employed there is a greater likelihood of side or competing reaction simply because there are more components in the system.

The present invention makes use of the discovery that the most efficient way to prepare alpha-substituted acyl compounds, particularly alpha-chloro acyl chlorides and acyl esters, is to begin with the corresponding carboxylic acid chloride.

The Hell-Volhard-Zelinksy (HVZ) alpha-bromination of carboxylic acids was discovered a century ago. This was based upon the observation that in the presence of a small amount of phosphorus, aliphatic carboxylic acids react smoothly with bromine to yield a compound in which the alpha-hydrogen has been replaced by a bromine substituent. Only recently has work related to regiospecific halogenation of acyl compounds focused upon the alpha-substitution of halogens other than bromine, and in particular to extending the HVZ reaction to alpha-chloro substitution. It was then quickly appreciated that the propensity of chlorine to undergo competing free radical reactions under HVZ conditions required the development of specialized procedure that would favor the ionic alpha-substitution process. See Little, Saxton, et al., *Journal of the American Chemical Society* 91 7098 (1969); U.S. Pat. No. 3,584,036 to Saxton, et. al., both of which relate to the solution of this problem.

Ogata, et. al., have developed a procedure which employs the addition of gaseous chlorine to a neat aliphatic acid at 140° C. in the presence of a strong acid catalyst and oxygen. Ogata suggests that the preferred catalyst is chlorosulfonic acid (10 mol % of the carboxylic acid) in combination with the oxygen gas. See Ogata, et al., *J. Org. Chem.*, 40 2960 (1975); Ogata, et al., *Tetrahedron* 26 5929 (1970); Ogata, et al., *Nippon Kagaku Kaishi* 1517 (1975) [Chem. Abstr. 83 178239 (1975)]; Ogata, et al., Japanese Patent 75-135024; Ogata, et al., Japanese Patent 74-24913. The method works particularly well for short chain ($C_2$–$C_6$) carboxylic acids. However, for chain lengths greater than $C_6$, the reaction is adequate, but sub-optimal. There is no suggestion here of halogenating acyl halide starting materials.

Crawford, U.S. Pat. No. 4,148,811, issued Apr. 10, 1979; U.S. Pat. No. 4,368,140, issued Jan. 11, 1983; *J. Org. Chem.* 48 1364 (1983); describes the regiospecific halogenation of long chain, as well as short chain, carboxylic acids, carboxylic acid halides, and acid anhydrides, employing a modification of Ogata's reaction. The major change is the use of a free radical inhibitor, such as 7,7,8,8-tetracyanoquinodimethane (TCNQ), in place of the oxygen gas. This change (TCNQ at 0.5 mol% in place of the oxygen) resulted in an improved reaction that was unaffected by chain length. (As stated above the use of oxygen and chloranil as taught by Ogata does not perform well on chain length greater than about $C_6$.) While Crawford states that this system can be used with the carboxylic acid, acid halide and acid anhydride, he states that temperatures above 130° C. must be employed if elemental chlorine is used as the halogen source. He also describes the many quinone or "quinone-like" structures which can be used as free radical inhibitors.

U.S. Pat. No. 3,880,923, Scheider, et al., issued Apr. 29, 1975, describes an improved process for the production of alpha-chloro-carboxylic acid chlorides by reacting a carboxylic acid chloride with chlorine at an elevated temperature in the presence of sulfuric acid.

U.S. Pat. No. 4,169,847, Degischer, issued Oct. 2, 1979, describes an improved process for the production of alpha-chloro-alkanoyl chlorides by reacting alkanoyl chlorides with chlorine at an elevated temperature in the presence of chlorosulphonic acid as a catalyst.

U.S. Pat. No. 3,152,055, Katzschmann, issued Oct. 6, 1964, describes production of aromatic chlorocarboxylic acid chlorides by using an ester as a starting material.

The methods of the present invention are simpler and more efficient, and possesses the following advantages versus those described in the art-disclosed processes: The reaction takes place under less rigorous conditions particularly when using elemental chlorine, goes more quickly, yields less alpha,alpha-dichloro material (and other products of competing reactions), and works efficiently regardless of the chain length of the starting material.

In particular, the present invention provides a marked improvement over the processes disclosed in U.S. Pat. Nos. 3,584,036; 4,148,811; and 4,368,140; discussed above.

With respect to the processes described by Crawford, the present method allows the use of elemental chlorine at temperatures significantly below 130° C. This is accomplished by employing the carboxylic acid halide, particularly the carboxylic acid chloride, as the starting material. Certain of the present methods allow excellent results to be obtained by employing commercial antioxidants in place of the more expensive free radical inhibitors of Crawford if the carboxylic acid chloride is used as a starting material; elemental chlorine and lower temperatures may also be employed.

With respect to the processes described by Ogata, the present method is made more efficient by beginning with the carboxylic acid halide, particularly the carboxylic acid chloride. This means that significantly less rigorous conditions may be employed. For example, if chloranil is employed as a free radical inhibitor in a process which begins with the free acid, and in a process which begin with the acid chloride, a higher yield can be obtained with a lower reaction temperature by employing the acid chloride (i.e., by following the teachings of the present invention).

The same is true if air or elemental oxygen are employed. If the acid chloride is used as the starting material and air or elemental oxygen are employed alone (without the free radical inhibitors employed by Ogata and Crawford, chloranil or TCNQ), the methods above can be run with equivalent results.

SUMMARY OF INVENTION

The process of the present invention comprises a method of producing alpha-chloro acyl chlorides comprising contacting an acyl chloride with a chlorine source at a temperature of about 75° C. to about 125° C. in the presence of (i) an effective amount of an auxiliary acidic agent and (ii) an effective amount of a food grade antioxidant and optionally (iii) an effective amount of oxygen or air.

See also co-pending U.S. patent applications entitled "Alpha Chlorination Process Employing Cyanoquinones" and "Alpha Chlorination Process Employing Air or Elemental Oxygen", James E. Thompson, Ser. Nos. 625,938 and 625,921, both filed June 29, 1984; incorporated herein by reference.

DETAILED DESCRIPTION OF THE INVENTION

The present invention encompasses an improved process for chlorinating acyl halides. The acyl chlorides used herein are characterized in that they contain at least one reactive hydrogen substituent at the alpha or 2-position. It is this hydrogen substituent which is displaced during the process of the present invention.

In the practice of this invention employing cyanoquinones, the acyl chloride is contacted with a chlorine source in the presence of an effective amount of an acidic auxiliary agent and an effective amount of a cyanoquinone material. This process is carried out at a temperature of about 75° C. to about 125° C.

In the practice of this invention employing antioxidants, the acyl chloride is contacted with a chlorine source in the presence of an effective amount of an acidic auxiliary agent and an effective amount of a food grade antioxidant material. This process is carried out at a temperature of about 75° C. to about 125° C.

In the practice of this invention employing air or oxygen alone, the acyl chloride is contacted with a chlorine source in the presence of an effective amount of an acidic auxiliary agent and air or elemental oxygen. This process is carried out at a temperature of about 75° C. to about 125° C.

The methods of the present invention may be employed to replace the alpha or 2-hydrogen substituent of any acyl halide with any halogen. However, as is well known, bromination, iodination, and particularly fluorination, reactions must be carried out under special conditions. Such reactions are therefore not contemplated in the practice of the present invention. Thus, while the present invention is particularly useful for both chlorinating and brominating acyl halides, on an industrial scale the processes of the present invention are particularly useful for chlorination reactions.

Thus, by the term "chlorination" or "chlorinating" herein is meant replacing the alpha or 2-hydrogen substiuent of any acyl chloride with a chlorine; however, the processes herein are useful for conducting bromination reactions.

By the term "acyl chloride" herein is meant compounds of the formula

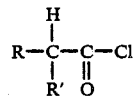

wherein R and R' are H or the same or different hydrocarbyl substituents having from about 1 to about 28 carbon atoms.

The processes of the present invention are particularly useful in chlorinating the acid (acyl) chlorides of octanoic, nonanoic, decanoic (capric), dodecanoic (lauric), tetradecanoic (myristic), hexadecanoic (palmitic), and octadecanoic (stearic) acids.

By the term "effective amount" of some material, component or agent, as that term is used herein, is meant a sufficient amount of that material, component or agent is present to direct the chlorination reaction regiospecifically such that it occurs almost exclusively at the alpha or 2-position of the acyl chloride.

By "comprising" herein is meant that various other compatible materials may be present in the reaction mixtures during the chlorination process. These materials and their levels may be selected such that they do not adversely affect the regiospecificity of the chlorination reaction. For example, various solvents or solvent mixtures may be optionally employed.

All percentages used herein are on a mol basis, unless otherwise specified.

ACIDIC AUXILIARY AGENTS

The acidic auxiliary agents used in the practice of the present invention include many of the common acidic materials known in the art for use in chlorination reactions. Such materials include both Lewis acids and inorganic protic acids which are stronger acids than hydrocarbyl carboxylic acids. Such acidic auxiliary agents include, without limitation, $PBr_3$, $PCl_3$, thionyl chloride, sulfuryl chloride, oxalyl chloride, sulfonyl chloride, $PCl_5$, phosgene, fluorosulfonic acid, chlorosulfonic acid, and trifluoromethanesulfonic acid. Chlorosulfonic acid is preferred.

It will be appreciated that the acyl halides themselves are not operative in the practice of this invention as acidic auxiliary agents inasmuch as it would then require the separation of the alpha-chlorinated acidic auxiliary agent from the material undergoing the desired alpha-halogenation.

CYANOQUINONES

The cyanoquinone materials used herein are all members of a well-known class of compounds. They have been associated with the synthesis of alpha-halogenated fatty acids, and have also been the subject of intensive study as electrically-conductive organic solids. Reviews of the preparation and properties of these materials and related materials can be found in the articles by Wheland, et al., *J. Amer. Chem Soc.* 98 3916 (1976); and Wheland, et al., *J. Org. Chem.* 40 3101 (1975); both incorporated herein by reference. The use of these materials as free radical inhibitors is described in detail in U.S. Pat. No. 4,148,811, issued Apr. 10, 1979; U.S. Pat. No. 4,368,149, issued Jan. 11, 1983; J. Org. Chem. 48 1364 (1983); all incorporated herein by reference.

A particularly useful synthesis is described by Crawford in "A Practical Synthesis of 7,7,8,8-Tetracyanoquinodimethane", *J. Org. Chem.* 48, 1366 (1983); incorporated herein by reference. In general, the cyanoquinones useful herein are characterized by the moiety

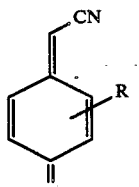

where R can be H or one or more substituent groups, e.g., halogen, alkyl, alkoxy, thioalkyl, CN, etc., as described by Wheland, et al., above.

The preferred cyanoquinones are the tetracyanoquinodimethane ("TCNQ") compounds of the formula

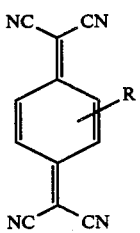

where R is as above.

Highly preferred cyanoquinone materials useful in the processes of the present invention include 7,7,8,8-tetracyanoquinodimethane ("TCNQ"), hexacyanobutadiene ("HCBC") and tetracyanonaphthoquinodimethane ("TNAP"). These can be depicted as follows:

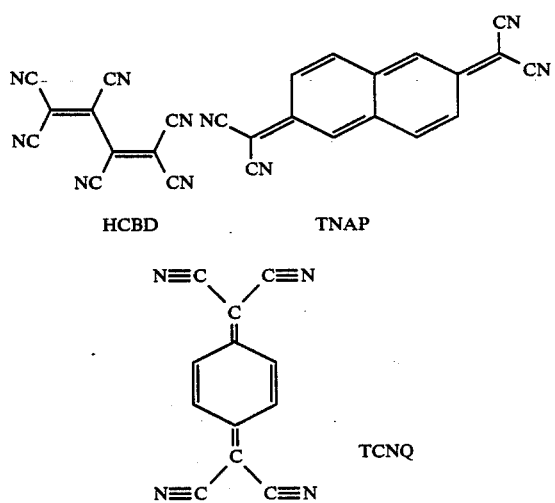

Tetracyanoquinodimethane ("TCNQ"), hexacyanobutadiene ("HCBC") and tetracyanonaphthoquinodimethane ("TNAP") can all be prepared according to conventional, art-disclosed techniques, including those discussed by Wheland, et al., as described above.

It should be noted that HCBD is not, in a technical sense, a formal quinone structure. However, its extended conjugated system of electrons gives it "quinone-like" characteristics. It has therefore come to be considered a cyanoquinone in the art; it is so considered within the present invention.

The most preferred catalyst system herein comprises a mixture of TCNQ and chlorosulfonic acid. Various ratios of these materials can be employed, but a ca. 1:5–1:50 mole ratio of TCNQ:ClSO$_3$H is convenient.

The most preferred chlorination reagent herein comprises gaseous or liquid elemental chlorine and the aforesaid mixture of TCNQ and chlorosulfonic acid. Of course, the chlorine in this reagent is replenished as it is exhausted during the reaction. Replenishment of the chlorine is most conveniently carried out by bubbling gaseous chlorine into the reaction mixture.

In a highly preferred embodiment of the present invention, the above catalyst system is used in combination with air or elemental oxygen. Air or elemental oxygen is bubbled through the reaction mixture preferably at a rate which achieves saturation in the reaction mixture.

The chlorination reaction of this invention is carried out by contacting the acyl chloride compound with the chlorine or chlorine source in the presence of a cyanoquinone material and acidic auxiliary agent at a temperature of about 75° C. to about 125° C.

In particular, chlorination reactions using elemental chlorine as the chlorine are carried out at temperatures of about 75° C. to about 125° C., preferably at temperatures with the range from about 100° C. to about 110° C. Bromination and iodination reactions are carried out under similar temperature conditions.

The process herein can be carried out in the presence or absence of inert solvents. Preferably, the reaction is carried out without the use of solvents, as this is both convenient and economical on a commerical scale. Indeed, the use of solvents can lead to undesirable side-reactions involving chlorination of many of the common hydrocarbon solvents. Under the reaction temperatures specified hereinabove, the acyl chloride compounds are liquids and are quite convenient to use in that state without additional solvents.

Typical use concentrations of the cyanoquinones relative to the acyl chloride compounds are 0.01–10.0 mole percent, preferably 0.05–5.0 mole percent, most preferably 0.05–0.5 mole percent.

Typical use concentrations of the acidic auxiliary agents relative to the acyl chloride compounds are 0.1–10 mole percent, preferably 1.0–5 mole percent.

ANTIOXIDANTS

It has also been discovered that certain antioxidants can be employed in the reaction of the present invention. Since many antioxidants work by inhibiting or interrupting the propagation step in the oxidation process, it was postulated (and confirmed) that these same agents would work in the same fashion, i.e., as free radical inhibitors, in the processes of the present invention.

Useful antioxidants include commercially available food grade antioxidants, especially the hindered phenols and secondary alkylaryl- and diarylamines. For example, compounds of the general formula (X)

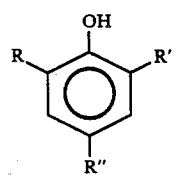

where R and R' are the same or different alkyl groups, and preferably t-butyl, are preferred. Also preferred are the bisphenols, such as those of the general formulae (XI) and (XII)

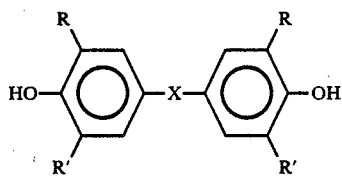 (XI)

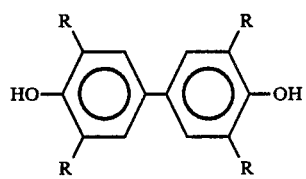 (XII)

wherein X is $CH_2$, $CHR_1$, $CR_1R_2$, or S, wherein $R_1$ and $R_2$ are as described for R and R' above.

Preferred antioxidants include butylated hydroxyanisole (BHA), butylated hydroxytoluene (BHT), t-butyl hydroquinone (TBHQ) propyl gallate (PG), and 6-ethoxy-1,2-dihydro-2,2,4-trimethylquinoline.

Particularly preferred antioxidants include butylated hydroxyanisole (BHA), butylated hydroxytoluene (BHT), and propyl gallate (PG). Mixtures of all the above may also be employed.

The preferred catalyst systems herein comprise mixtures of TBHQ, BHA, or BHT, and chlorosulfonic acid. Various ratios of these materials can be employed, but a 1:5–1:50 mole ratio of antioxidant:$ClSO_3H$ is convenient.

The most preferred chlorination reagent herein comprises gaseous or liquified elemental chlorine and the aforesaid mixtures of antioxidant and chlorosulfonic acid. Of course, the chlorine in this reagent is replenished as it is exhausted during the reaction. Replenishment of the chlorine is most conveniently carried out by bubbling gaseous chlorine into the reaction mixture.

The chlorination reaction of this invention is carried out by contacting the acyl chloride compound with the chlorine or chlorine source in the presence of material and acidic auxiliary agent at a temperature of about 75° C. to about 125° C.

In a highly preferred embodiment of the present invention, the above catalyst system is used in combination with air or elemental oxygen. Air or elemental oxygen is bubbled through the reaction mixture preferably at a rate which achieves saturation in the reaction mixture.

In particular, chlorination reactions using elemental chlorine as the chlorine are carried out at temperatures of about 75° C. to about 125° C., and preferably at temperatures with the range from about 100° C. to about 110° C. Bromination and iodination reactions are carried out under similar temperature conditions.

The process herein can be carried out in the presence or absence of inert solvents. Preferably, the reaction is carried out without the use of solvents, and this is both convenient and economical on a commercial scale. Indeed, the use of solvents can lead to undesirable side-reactions involving chlorination of many of the common hydrocarbon solvents. Under the reaction temperatures specified hereinabove, the acyl chloride compounds are liquids and are quite convenient to use in that state without additional solvents.

Typical use concentrations of the antioxidants relative to the acyl chloride compounds are 0.1–10.0 mole percent, preferably 0.1–5.0 mole percent, most preferably 0.5–0.5 mole percent.

Typical use concentrations of the acidic auxiliary agents relative to the acyl chloride compounds are 0.1–10 mole percent, preferably 1.0–2.5 mole percent.

The following examples illustrate the practice of the present invention but are not intended to be in any way limiting thereof.

AIR/OXYGEN ALONE

As has been described above in detail, it has been discovered that many known alpha chlorination reactions can be improved (better yields under less rigorous conditions) by using acyl chloride starting materials. It has also been discovered that the increased efficiency which results from the methods employing acyl chloride starting materials allows this reaction to be conducted just as efficiently as known methods (Ogata, Crawford, discussed above) without the use of antioxidants or cyanoquinones.

Accordingly, the process of the present invention comprises a method of producing alpha-chloro acyl chlorides in the absence (less than 0.005 mol%) of antioxidants or cyanoquinones comprising contacting an acyl chloride with a chlorine source at a temperature of about 75° C. to about 125° C. in the presence of (i) an effective amount of an auxiliary acidic agent and (ii) an effective amount of elemental oxygen or air. (See Trial 14 of Example IV.)

The preferred catalyst systems herein comprises a mixture of air and chlorosulfonic acid. Various ratios of these materials can be employed, but a system which passes air through the reaction mixture such that saturation is achieved is preferred and convenient.

The most preferred chlorination reagent herein comprises gaseous or liquid elemental chlorine and the aforesaid mixtures of air or oxygen and chlorosulfonic acid. Of course, the chlorine in this reagent is replenished as it is exhausted during the reaction. Replenishment of the chlorine is most conveniently carried out by bubbling gaseous chlorine into the reaction mixture.

The chlorination reaction of this invention is carried out by contacting the acyl chloride compound with the chlorine or chlorine source in the presence of material and acidic auxiliary agent at a temperature of about 75° C. to about 125° C.

In particular, chlorination reactions using elemental chlorine as the chlorine are carried out at temperatures of about 75° C. to about 125° C., and preferably at temperatures with the range from about 100° C. to about 110° C. Bromination and iodination reactions are carried out under similar temperature conditions.

The process herein can be carried out in the presence or absence of inert solvents. Preferably, the reaction is carried out without the use of solvents, and this is both convenient and economical on a commercial scale. Indeed, the use of solvents can lead to undesirable side-reactions involving chlorination of many of the common hydrocarbon solvents. Under the reaction temperatures specified hereinabove, the acyl chloride compounds are liquids and are quite convenient to use in that state without additional solvents.

The following examples illustrate the practice of the present invention but are not intended to be in any way limiting thereof.

EXAMPLE I

Alpha-Chlorination of Nonanoyl Chloride in the Presence of Tetracyanoquinodimethane (TCNQ)

A 1.0 liter five-necked round-bottomed flask was fitted with a mechanical stirrer, thermometer, dry ice condenser (with a gas exit tube) and two fritted glass dispersion tubes which extended to near the bottom of the flask. The two dispersion tubes were connected via PVC tubing to a Y connector and thence to a chlorine source. An in-line flow meter was employed.

The flask was charged with 487 g (2.75 moles) of nonanoyl chloride and was immersed in an oil bath maintained at 100° C. TCNQ (1.8 g, 8.8 millimoles, 0.32 mole %) and chlorosulfonic acid (9.6 g, 82.5 millimoles, 3 mole %) were added and the chlorine flow was started (time, t=0). The flow rate was 2.5 liters/min (900 ml/min/mole).

A mild exotherm occurred which gradually raised the temperature to 120° C. It held there until near the end of the reaction. At t=25 min, an additional 1.0 g (4.9 millimoles, 0.18 mole %) of TCNQ was added. At t=40 min (T=120° C.), chlorine began to reflux more rapidly and the temperature began to fall. By t=49 min, the temperature had dropped to 90° C. and the chlorine flow was stopped. The oil bath was removed. Aliquots subsequently showed that the reaction was complete by t=45 min.

The reaction mixture was degassed and the alpha-chloro acid chloride was distilled directly from the reaction flask. A main fraction, 494 g (85%), b.p. 69°-70° C. (0.5 mm) was obtained. This fraction was 99% pure by gas chromatography. Other, less pure distillation fractions contained an additional 5-6% of the desired product.

Substantially similar results are obtained when the above reaction is conducted replacing the TCNQ, in whole or in part, with hexacyanobutadiene ("HCBC") and tetracyanonaphthoquinodimethane ("TNAP").

The process of EXAMPLE I is carried out using the acid (acyl) chlorides of octanoic, decanoic (capric), dodecanoic (lauric), tetradecanoic (myristic), hexadecanoic (palmitic), and octadecanoic (stearic) acids. Substantially similar results (high yields) are obtained.

Substantially similar results are obtained when the chlorosulfonic acid is replaced, in whole or in part, with $PBr_3$, $PCl_3$, thionyl chloride, sulfuryl chloride, oxalyl chloride, sulfonyl chloride, $PCl_5$, phosgene, fluorosulfonic acid, and trifluoromethanesulfonic acid.

EXAMPLE II

Alpha-Chlorination of Octanoyl Chloride in the Presence of Air and Tetracyanoquinodimethane (TCNQ)

A 100 ml four-necked round-bottomed flask equipment for magnetic stirring was fitted with a thermometer, dry ice condenser (with a gas exit tube) and two gas inlet tubes. The inlet tubes each had 3 mm diameter openings and extended to near the bottom of the reaction flask. One was connected via PVC tubing to a chlorine source containing an in-line flow meter. The other was similarly connected to a compressed air source.

The flask was charged with 52.2 g (320 millimoles) of octanoyl chloride and was immersed in an oil bath maintained at 100° C. When the acid chloride temperature reached 100° C., TCNQ (0.033 g, 0.16 millimoles, 0.05 mole %) and chlorosulfonic acid (1.2 g, 10 millimoles, 3.1 mole %) were added. Flows of air and chlorine, each at 400 ml/min (1250/ml/min/mole), were then begun (time t=0).

The reaction temperature gradually rose to 116° C. At t=25 min, chlorine reflux began to accelerate and the reaction was stopped at t=30.5 min.

For convenient yield determination, the acid chloride was converted to methyl ester by the addition of 150 ml of methanol. This mixture was dissolved in 300 ml of methylene chloride and was washed successively with 100 ml portions of water (twice) saturated sodium bicarbonate solution (once) and water again (twice). The organic solution was dried overnight, filtered and distilled to give 57.0 g (93%) of distillate, b.p. 72° (0.3 mm). By gas chromatography, the product consisted of 97.7% monochloro- and 2.3% dichloro octanoate.

Substantially similar results are obtained when the TCNQ is replaced, in whole or in part, with hexacyanobutadiene ("HCBC") and tetracyanonaphthoquinodimethane ("TNAP").

The process of EXAMPLE II is carried out using the acid (acyl) chlorides of nonanoic, decanoic (capric), dodecanoic (lauric), tetradecanoic (myristic), hexadecanoic (palmitic), and octadecanoic (stearic) acids. Substantially similar results (high yields) are obtained.

Substantially similar results are obtained when the chlorosulfonic acid is replaced, in whole or in part, with $PBr_3$, $PCl_3$, thionyl chloride, sulfuryl chloride, oxalyl chloride, sulfonyl chloride, $PCl_5$, phosgene, fluorosulfonic acid, and trifluoromethanesulfonic acid.

EXAMPLE III

Alpha-Chlorination of Nonanoyl Chloride in the Presence of t-Butylhydroquinone (TBHQ) and Air A 1.0 liter five-necked round-bottomed flask was fitted with a mechanical stirrer, thermometer, dry ice condenser (with a gas exit tube) and two fritted glass dispersion tubes which extended to near the bottom of the flask. One of the tubes was connected via PVC tubing to a chlorine source containing an in-line flow meter. The other was similarly connected to a compressed air source.

The flask was charged with 487 g (2.75 moles) of nonanoyl chloride and was immersed in an oil bath maintained at 100° C. When the temperature of the acid chlorine reached 100° C., TBHQ (1.3 g, 7.8 millimoles, 0.28 mole %) and chlorosulfonic acid (9.6 g, 82.5 millimoles, 3 mole %) were added. Flows of chlorine and air, each at 350 ml/min, were then begun (t=0).

A mild exotherm occurred which gradually raised the temperature to 124° C. It held there until near the end of the reaction. At t=25 min, an additional 1.0 g (6.0 millimoles, 0.22 mole %) of TBNQ was added. At t=39 min (T=117° C.), chlorine began to reflux more rapidly and the temperature began to fall. Gas flow was stopped and the oil bath was removed. An aliquot showed that the reaction mixture consisted of 92% alpha-chloronanonyl chloride.

The reaction mixture was degassed and the alpha-chloro acid chloride was distilled directly from the reaction flask. A main fraction, 492 g (85%), b.p. 69°-70° C. (0.5 mm) was obtained. This fraction was 93% pure by gas chromatography. An additional 7-8% of the desired product was present in subsequent, less pure fractions.

Substantially similar results are obtained when the TBHQ is replaced, in whole or in part, with butylated hydroxyanisole (BHA), butylated hydroxytoluene (BHT), t-butyl hydroquinone (TBHQ) propyl gallate (PG), and 6-ethoxy-1,2-dihydro-2,2,4-trimethylquinoline.

The process of EXAMPLE III is carried out using the acid (acyl) chlorides of octanoic, decanoic (capric), dodecanoic (lauric), tetradecanoic (myristic), hexadecanoic (palmitic), and octadecanoic (stearic) acids. Substantially similar results (high yields) are obtained.

Substantially similar results are obtain when the chlorosulfonic acid is replaced, in whole or in part, with $PBr_3$, $PCl_3$, thionyl chloride, sulfuryl chloride, oxalyl chloride, oxalyl chloride, sulfonyl chloride, $PCl_5$, phosgene, fluorosulfonic acid, and trifluoromethanesulfonic acid.

In the following Example, the following abbreviations are employed. For reactants (starting materials), "NC" represents nonanoyl chloride; "OC" represents octanoyl chloride; "SC" represents stearoyl chloride; and "NA" represents nonanoic acid. "CSA" is used for the auxiliary acidic agent chlorosulfonic acid.

Time is time in minutes. Products: Products A represents percent of alpha-chloro product; B represents percent of starting material (reactant) remaining; C represents the percent of alpha, alpha-dichloro material produced; D represents all other materials, including free radical product. A single asterisk (*) represents a flow rate for that gas of 625 ml/min/mol; () represents a rate of 1250 ml/min/mol; (*) represents a rate of 156 ml/min/mol.

EXAMPLE IV

What is claimed is:

1. A process for preparing an alpha-chloro acyl chloride comprising contacting an acyl chloride of an acid selected from the group consisting of octanoic acid, nonanoic acid, decanoic acid, dodecanoic acid, tetradecanoic acid, hexadecanoic acid and octadecanoic acid, with a chlorine source at a temperature of about 75° C. to about 125° C. in the presence of
   (i) an effective amount of auxiliary acidic agent and
   (ii) an effective amount of a food-grade antioxidant.

2. A process according to claim 1 wherein the chlorine source is elemental chlorine gas.

3. A process according to claim 2 wherein the auxiliary acidic agent is selected from the group consisting of $PBr_3$, $PCl_3$, thionyl chloride, sulfuryl chloride, oxalyl chloride, sulfonyl chloride, $PCl_5$, phosgene, fluorosulfonic acid, chlorosulfonic acid, and trifluoromethanesulfonic acid, and mixtures thereof.

4. A process according to claim 3 wherein the auxiliary acidic agent is chlorosulfonic acid.

5. A process according to claim 4 wherein the food grade antioxidant is selected from the group consisting of butylated hydroxyanisole, butylated hydroxytoluene, t-butyl hydroquinone, propyl gallate, 6-ethoxy-1,2-dihydro-2,2,4-trimethylquinoline, and mixtures thereof.

6. A process according to claim 5 wherein the antioxidant is selected from the group consisting of butylated hydroxyanisole, butylated hydroxytoluene, t-butyl hydroquinone, propyl gallate, and mixtures thereof.

7. A process according to claim 2 wherein the reaction temperature is about 100° C. to about 110° C.

8. A process according to claim 2 wherein the reaction is conducted in the presence of air or elemental oxygen.

9. A process for preparing an alpha-chloro acyl chloride comprising contacting an acyl chloride of an acid

Chlorination of Acid Chlorides

| Trial | Reactant | $Cl_2$ | T° C. | CSA | SYSTEM | TIME | A | B | C | D |
|---|---|---|---|---|---|---|---|---|---|---|
| 1 | NC | 625 | 150 | 3.1 | 0.5 TCNQ | 40' | 94 | 0 | 3.8 | 1.1 |
| 2 | NC | 625 | 100 | 3.1 | 0.5 TCNQ + 0.1 @ 30' | 45' | 97 | 1 | 2.5 | Nil |
| 3 | NC | 900 | 100 | 3.1 | 0.3 TCNQ + 0.2 @ 25' | 45' | 99 | 0 | 1.3 | Nil |
| 4 | NC | 1250 | 100 | 3.1 | 0.5 TCNQ + 0.15 @ 20' | 25' | 92 | 4 | 3.5 | Nil |
| 5 | NC | 1250 | 100 | 3.1 | 0.25 TCNQ | 30' | 95 | 1 | 4.3 | Nil |
| 6 | NC | 1250 | 100 | 3.1 | 0.05 TCNQ | 30' | 96 | 1 | 3.2 | 0.2 |
| 7 | NC | 1250 | 100 | 3.1 | 0.01 TCNQ | 30' | 95 | 0 | 2.5 | 2.3 |
| 8 | NC | 1250 | 100 | 3.1 | 0.01 TCNQ + Air* | 30' | 98 | 0 | 2.2 | Nil |
| 9 | NC | 1250 | 100 | 3.1 | 0.05 TCNQ + Air* | 31' | 98 | 0 | 2.2 | Nil |
| 10 | NC | 1250 | 100 | 3.1 | 0.5 M Chloranil Air* | 35' | 98 | 0 | 2.0 | 0.3 |
| 11 | NC | 1250 | 100 | 3.1 | 0.5 M TBHQ + $O_2$** | 30' | 97 | 0 | 1.9 | 0.5 |
| 12 | NC | 1250 | 100 | 3.1 | 0.5 M TBHQ + Air* | 30' | 95 | 2 | 2.5 | 0.7 |
| 13 | NC | 1250 | 100 | 3.1 | 0.5 M BHT + $O_2$** | 35' | 95 | 0 | 3.1 | 1.8 |
| 14 | NC | 1250 | 100 | 3.1 | $O_2$** | 30' | 93 | 1 | 2.0 | 3.3 |
| 15 | OC | 1250 | 100 | 1.0 | 0.05 TCNQ + Air* | 29' | 72 | 20 | 7.4 | Nil |
| 16 | NC | 1250 | 150 | 0 | 0.5 M TCNQ | 25' | 51 | 38 | 10 | Nil |
| 17 | NA | 625 | 150 | 3.1 | 0.5 M TCNQ 0.15 M TCNQ @ 30' | 45' | 94 | 0 | 2.4 | 3.5 |
| 18 | NC | 1250 | 100 | 3.1 | 0.1 M Chloranil + Air* | 40' | 93 | 0 | 2.3 | 4.9 |
| 19 | SC | 900 | 100 | 3.1 | 0.5 M TCNQ + Air* | 50' | 96 | 1 | 3 | Nil |
| 20 | SC | 900 | 100 | 3.1 | 0.05 M TCNQ + Air* | 50' | 70 | 23 | 5.8 | Nil |
| 21 | SC | 900 | 100 | 3.1 | 0.5 M Chloranil + Air* | 50' | 96 | 1 | 2.5 | Nil |
| 22 | SC | 1250 | 100 | 3.1 | None | 40' | 65 | 23 | 2 | 10 |
| 23 | OC | 1250 | 100 | 3.1 | BHT + Air*** | 65' | 95 | 0 | 1.8 | 3.3 |
| 24 | OC | 1250 | 100 | 3.1 | BHT | 30' | 68 | 5 | 1.7 | 30 | selected from the group consisting of octanoic acid, nonanoic acid, decanoic acid, dodecanoic acid, tetradecanoic acid, hexadecanoic acid and octadecanoic acid, with elemental chlorine gas at a temperature of about 75° C. to about 125° C. in the presence of
  (i) an effective amount of chlorosulfonic acid and
  (ii) an effective amount of an antioxidant selected from the group consisting of butylated hydroxyanisole, butylated hydroxytoluene, t-butyl hydroquinone, propyl gallate, and mixtures thereof.

10. A process according to claim 9 wherein the reaction temperature is about 100° C. to about 110° C.

11. A process according to claim 10 wherein the reaction is conducted in the presence of air or elemental oxygen.

12. A process according to claim 11 wherein the antioxidant is butylated hydroxyanisole.

13. A process according to claim 11 wherein the antioxidant is butylated hydroxytoluene.

* * * * *